US012540301B2

(12) United States Patent
Horii et al.

(10) Patent No.: US 12,540,301 B2
(45) Date of Patent: Feb. 3, 2026

(54) CELL CULTURE DEVICE

(71) Applicant: Sinfonia Technology Co., Ltd., Tokyo (JP)

(72) Inventors: Daichi Horii, Tokyo (JP); Yasumichi Mieno, Tokyo (JP); Haruki Takeuchi, Tokyo (JP)

(73) Assignee: Sinfonia Technology Co., Ltd., Tokyo (JP)

( * ) Notice: Subject to any disclaimer, the term of this patent is extended or adjusted under 35 U.S.C. 154(b) by 847 days.

(21) Appl. No.: 17/586,153

(22) Filed: Jan. 27, 2022

(65) Prior Publication Data

US 2022/0243161 A1 Aug. 4, 2022

(30) Foreign Application Priority Data

Feb. 4, 2021 (JP) ................................ 2021-016956

(51) Int. Cl.
*C12M 3/04* (2006.01)
*C12M 3/00* (2006.01)

(52) U.S. Cl.
CPC ............ *C12M 27/10* (2013.01); *C12M 23/48* (2013.01)

(58) Field of Classification Search
CPC ....... C12M 23/48; C12M 27/10; C12M 27/16
See application file for complete search history.

(56) References Cited

U.S. PATENT DOCUMENTS

2009/0137026 A1* 5/2009 Kan ....................... C12M 41/00 435/286.4
2020/0208087 A1 7/2020 Horii et al.

FOREIGN PATENT DOCUMENTS

| | | | | | |
|---|---|---|---|---|---|
| EP | 3674391 | A2 | | 7/2020 | |
| JP | 2003070464 | A | * | 3/2003 | C12M 27/10 |
| JP | 2004329045 | A | * | 11/2004 | C12M 23/12 |
| JP | 2005227070 | A | * | 8/2005 | |
| JP | 2020-103232 | A | | 7/2020 | |

OTHER PUBLICATIONS

Europe Patent Application No. 22153639.4, Extended European Search Report, dated Jul. 6, 2022.

* cited by examiner

*Primary Examiner* — Elizabeth A Robinson
*Assistant Examiner* — Jonathan E Lepage
(74) *Attorney, Agent, or Firm* — Kilpatrick Townsend & Stockton LLP

(57) ABSTRACT

A cell culture device includes: a base; a rotary table attached to the base; a container holding member attached to the rotary table and configured to hold a cell culture container; and a drive mechanism configured to rotatably drive the rotary table around a first axis and the container holding member around a second axis, wherein a liquid port to which a liquid tube is connected is arranged on an outer peripheral surface of the cell culture container, wherein a first predetermined portion of the liquid tube is positioned on the container holding member by a first positioning member, wherein a second predetermined portion of the liquid tube is positioned on the rotary table by a second positioning member, and wherein the first positioning member is rotatably attached to the container holding member.

16 Claims, 14 Drawing Sheets

CELL CULTURE DEVICE

CROSS-REFERENCE TO RELATED APPLICATION

This application is based upon and claims the benefit of priority from Japanese Patent Application No. 2021-016956, filed on Feb. 4, 2021, the entire contents of which are incorporated herein by reference.

TECHNICAL FIELD

The present disclosure relates to a cell culture device suitable for appropriately performing large-scale culture.

BACKGROUND

In a cell culture technique for culturing cells through the use of a cell culture container, a cell culture device that performs handling operations such as an operation of rotating the cell culture container and the like is used in order to introduce a culture solution seeded with cells into the cell culture container or recover the cells from the cell culture container (see, e.g., Patent Document 1).

The cell culture device of Patent Document 1 includes a drive mechanism for changing a posture of the cell culture container. The drive mechanism includes a base, a rotary table attached to the base and capable of rotating around a first axis X, a container holding member attached to the rotary table and capable of rotating around a second axis Y, a first drive part that rotationally drives the rotary table around the first axis X, a second drive part that rotationally drives the container holding member around the second axis Y, and a controller that controls these drive parts.

Therefore, by controlling the first drive part and the second drive part, it is possible to rotate the rotary table and/or the container holding member and to supply the culture solution to a liquid supply/drainage port of the cell culture container, or to recover the culture solution from the liquid supply/drainage port of the cell culture container.

PRIOR ART DOCUMENT

Patent Document

Patent Document 1: Japanese Patent Application Publication No. 2020-103232

In the cell culture device of Patent Document 1, a liquid supply/drainage tube for supplying and draining the culture solution is connected to the liquid supply/drainage port of the cell culture container. The rotary table and/or the container holding member is rotationally driven in a state in which the liquid supply/drainage tube is connected to the liquid supply/drainage port. A plurality of mutually spaced-apart portions of the liquid supply/drainage tube is positioned on the rotary table or the container holding member in order to prevent the liquid supply/drainage tube from being caught in the surroundings when the rotary table and/or the container holding member rotates. In that case, an extra length portion is formed between the portions of the liquid supply/drainage tube positioned on the rotary table and the portions of the liquid supply/drainage tube positioned on the container holding member so that the rotation of the rotary table and/or the container holding member is not restricted.

However, when the extra length portion of the liquid supply/drainage tube is made too long, there is a problem that the liquid supply/drainage tube may be caught in the surroundings during the rotation of the rotary table and/or the container holding member and may be torn or removed from the liquid supply/drainage port whereby the culture cannot be continued. When the extra length portion of the liquid supply/drainage tube is made too short, there is a problem that the liquid supply/drainage tube may be pulled during the rotation of the rotary table and/or the container holding member and may be removed from the liquid supply/drainage port or may be bent to be clogged whereby the culture cannot be continued.

SUMMARY

The present disclosure provides a cell culture device in which an extra length of a liquid tube connected to a cell culture container is properly set.

The present disclosure provides the following solutions.

A cell culture device according to the present disclosure includes: a base; a rotary table attached to the base and capable of rotating around a first axis; a container holding member attached to the rotary table and capable of rotating around a second axis, the container holding member being configured to hold a cell culture container; and a drive mechanism configured to rotationally drive the rotary table around the first axis and to rotationally drive the container holding member around the second axis, wherein a liquid port to which a liquid tube is connected is arranged on an outer peripheral surface of the cell culture container, wherein a first predetermined portion of the liquid tube, which is spaced apart by a predetermined length from a connection portion connected to the liquid port, is positioned on the container holding member by a first positioning member, wherein a second predetermined portion of the liquid tube, which is further spaced apart from the connection portion than the first predetermined portion, is positioned on the rotary table by a second positioning member, and wherein the first positioning member is rotatably attached to the container holding member.

With the configuration described above, by rotatably attaching the first positioning member for positioning the first predetermined portion of the liquid tube to the container holding member, it is possible to eliminate an extra length portion formed between the first predetermined portion and the second predetermined portion of the liquid tube. Therefore, in a case of supplying a reagent into the cell culture container or draining the reagent from the cell culture container, it is possible to prevent the extra length portion of the liquid tube connected to the liquid port from becoming too long, so that the culture can be continued properly even when the rotary table and/or the container holding member is rotationally driven in a state in which the liquid tube is connected to the liquid port.

In the cell culture device of the present disclosure, a third predetermined portion of the liquid tube, which is closer to the connection portion than the first predetermined portion, may be positioned on the container holding member by a third positioning member.

With the configuration described above, when the rotary table and/or the container holding member is rotationally driven in the state in which the liquid tube is connected to the liquid port, the direction of the first predetermined portion of the liquid tube, which is rotatably positioned on the container holding member by the first positioning member, is easily changed. Therefore, it is possible to easily eliminate the extra length portion formed between the first predetermined portion and the second predetermined portion of the liquid tube.

In the cell culture device of the present disclosure, the first predetermined portion and the third predetermined portion may be positioned on the same plane with respect to the container holding member.

With the configuration described above, the direction of the first predetermined portion of the liquid tube, which is rotatably positioned with respect to the container holding member by the first positioning member, is easily changed. Therefore, it is possible to further eliminate the extra length portion formed between the first predetermined portion and the second predetermined portion of the liquid tube.

In the cell culture device of the present disclosure, the drive mechanism may be configured to rotationally drive the rotary table and the container holding member so that in a liquid drainage operation for draining a reagent from the cell culture container, the reagent flowing out from the liquid port into the liquid tube flows in the liquid tube in a direction away from the liquid port under a gravitational force acting on the reagent.

With the configuration described above, it is possible to prevent the reagent from remaining in the liquid tube after the reagent is drained from the cell culture container.

BRIEF DESCRIPTION OF DRAWINGS

The accompanying drawings, which are incorporated in and constitute a part of the specification, illustrate embodiments of the present disclosure.

DETAILED DESCRIPTION

Reference will now be made in detail to various embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, systems, and components have not been described in detail so as not to unnecessarily obscure aspects of the various embodiments.

Hereinafter, embodiments of the present disclosure will be described with reference to the drawings.

Figure 1:
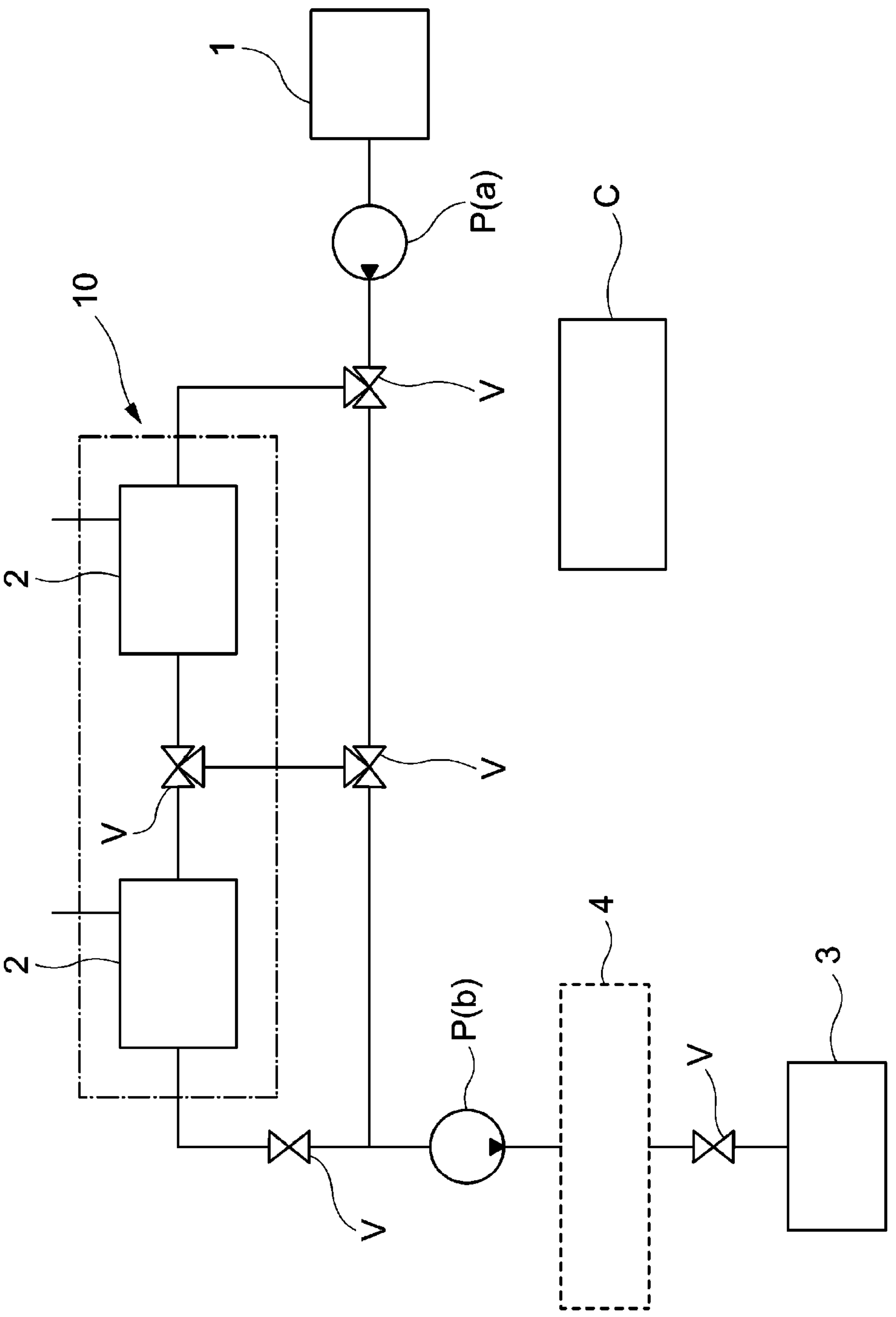
FIG. 1 is a schematic configuration diagram of a cell culture system according to an embodiment of the present disclosure.

FIG. 1 is a system diagram simply showing a cell culture system according to the present embodiment. The cell culture system includes a liquid storage part 1 such as, for example, a refrigerator or the like, a cell culture container 2, and a cell recovery part 3 that recovers cells cultured in the cell culture container 2. The liquid storage part 1, the cell culture container 2, and the cell recovery part 3 are connected by a sterile connector (not shown) at appropriate points. After an operation is started once after assembling the components, the inside of the system is maintained as a closed system line until the operation is completed, whereby entry of bacteria from the outside is prevented.

The liquid storage part 1 stores liquids such as a medium, various reagents and the like to be supplied to the cell culture container 2. The inside of the liquid storage part 1 is kept at a temperature of, for example, about 4 degrees C. required for refrigerating the medium and various reagents.

The cell culture container 2 has a shelf structure in which cells are cultured in a flat-developed medium. The cell culture container 2 is kept under a temperature environment of about 37 degrees C. in order to promote cell division.

The cell recovery part 3 recovers the cells in the liquid, which is taken out after culturing in the cell culture container 2. When necessary, an intermediate processing part 4 such as an analysis part that analyzes a state of cells and an adjustment part that adjusts a dilution degree of the suspension containing cells is interposed between the cell culture container 2 and the cell recovery part 3. All the lines in the intermediate processing part 4 also constitute the closed system line.

In the closed system line described above, there is constructed a system that automatically performs, without human intervention, a process of preparing liquids such as a medium and a reagent in the liquid storage part 1 and then transferring those liquids from the liquid storage part 1 to the cell culture container 2, a process of culturing cells in the cell culture container 2, a process of taking out the cultured cells from the cell culture container 2 and recovering the cells in the cell recovery part 3, and a process of performing, by the intermediate processing part 4, various intermediate processes on the liquids taken out from the cell culture container 2 before recovering the cells.

Therefore, valves V and pumps P (pump P(a) and pump P(b)) are connected to respective lines as needed. These valves V and pumps P are controlled by control commands from a controller C. The pump P(a) and the pump P(b) may be used for both pumping and suction applications.

Figure 2:
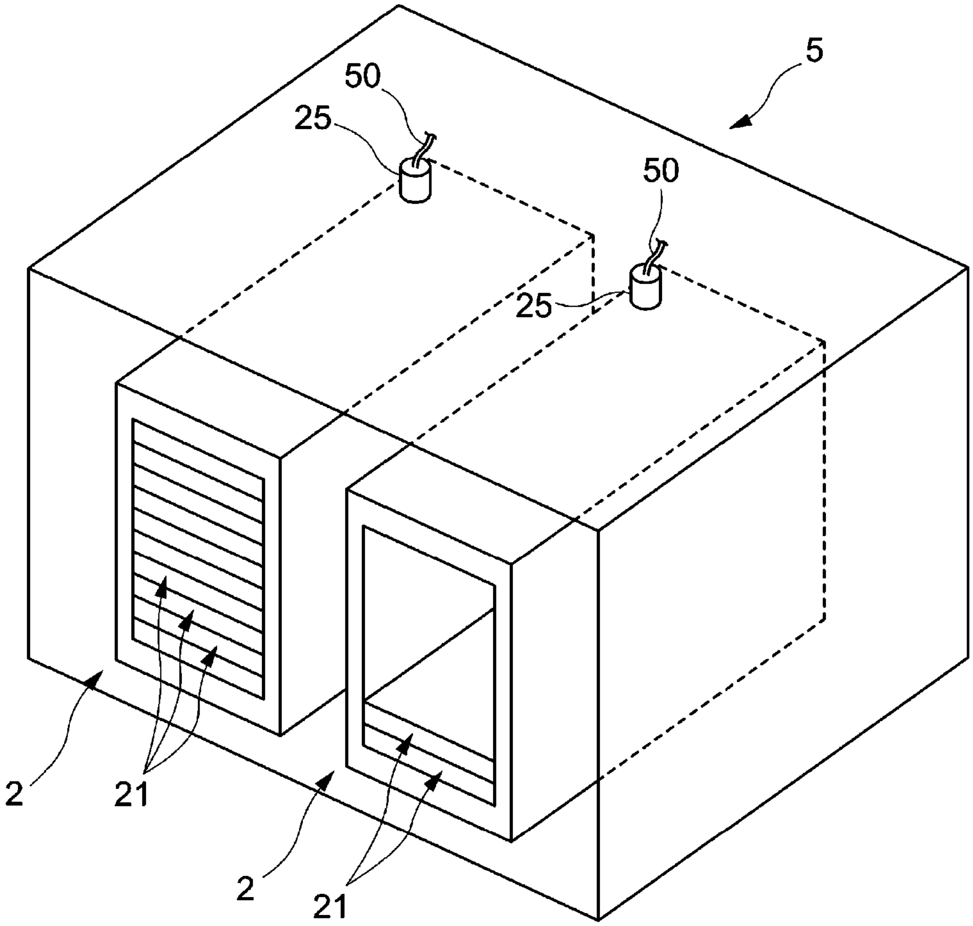
FIG. 2 is a diagram showing an incubator that accommodates a cell culture container in the cell culture system of FIG. 1.

In the present embodiment, in order to keep the cell culture container 2 at a predetermined temperature without breaking the closed system line, a cell culture device 10 including the cell culture container 2 and peripheral element parts is arranged in an incubator 5 as shown in FIGS. 1 and 2 while connecting the liquid supply/drainage tube 50 that constitutes a part of the closed system line.

As a result, the cell culture container 2 is spatially constrained. Therefore, in order to achieve a large amount of culture as much as possible, it is necessary to increase a culture rate in the cell culture container 2.

Therefore, in the present embodiment, the cell culture container 2 has a multi-stage shelf structure and adopts a configuration that increases a culture area as much as the number of shelves 21. Due to the multi-stage shelf structure, it is necessary to perform a process of distributing a liquid supplied from the outside to the respective shelves 21 and draining the liquid from the respective shelves 21 to the outside after the culture is completed. At that time, in order to reduce the number of connected lines of the closed system line as much as possible, a liquid supply/drainage port 25 that serves as both a supply liquid port and a drainage liquid port is provided in a housing of the cell culture container 2. The liquid supply/drainage port 25 is common to the respective shelves 21. By changing a posture of the cell culture container 2 in the incubator 5 while maintaining the closed system line state, it is possible to implement a liquid supply to the respective shelves 21 and a liquid drainage from the respective shelves 21.

Figure 3A:
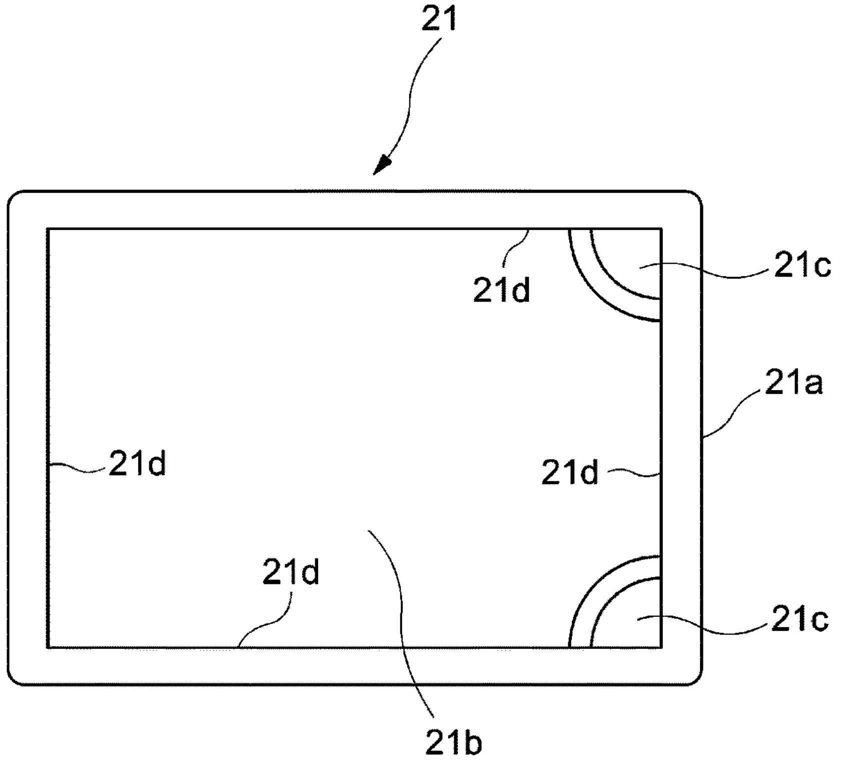
FIGS. 3A and 3B are diagrams showing a shelf structure of the cell culture container.
Figure 3B:
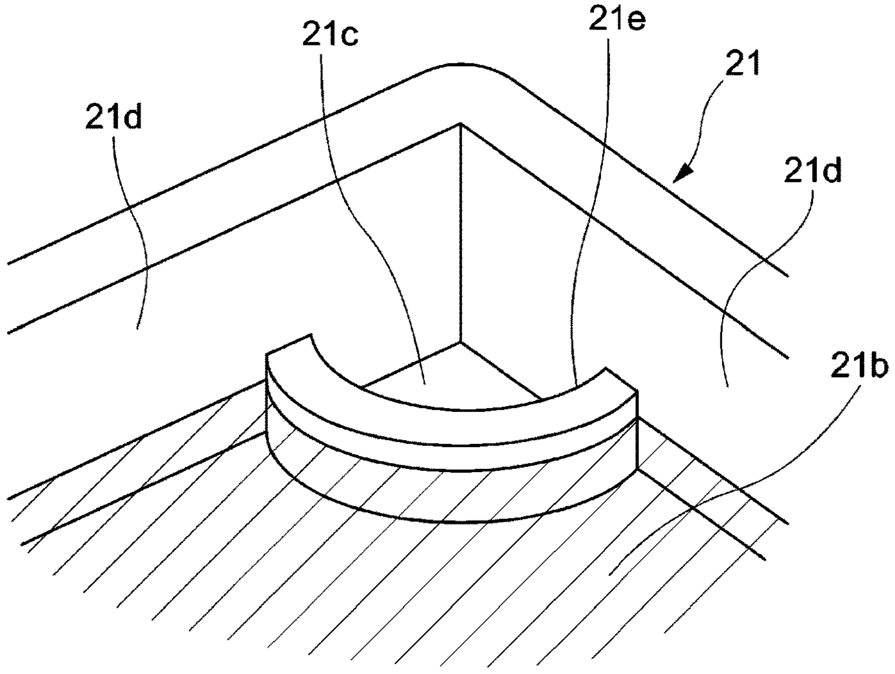

Specifically, as shown in FIGS. 3A and 3B, the cell culture container 2 is configured such that communication portions 21*c* are provided at corner portions on a side of one end edge 21*a* of each of the shelves 21 by cutting out a part of a shelf surface 21*b* so that the liquid can evenly enter respective shelf spaces, and the shelve spaces are partitioned by the shelf surface 21*b* and a side surface 21*d* in portions other than the communication portions 21*c*. At a boundary between the communication portion 21*c* and the shelf surface 21*b*, a vertical wall 21*e* having a lower height than the side surface 21*d* is provided so that the liquid is stored when the shelf surface 21*b* is in a horizontal state, and the liquid is drained when the shelf surface 21*b* is tilted or inverted. That is, the portion shown by hatching in FIG. 3B indicates a region where the liquid can be stored in the horizontal state.

Figure 4:
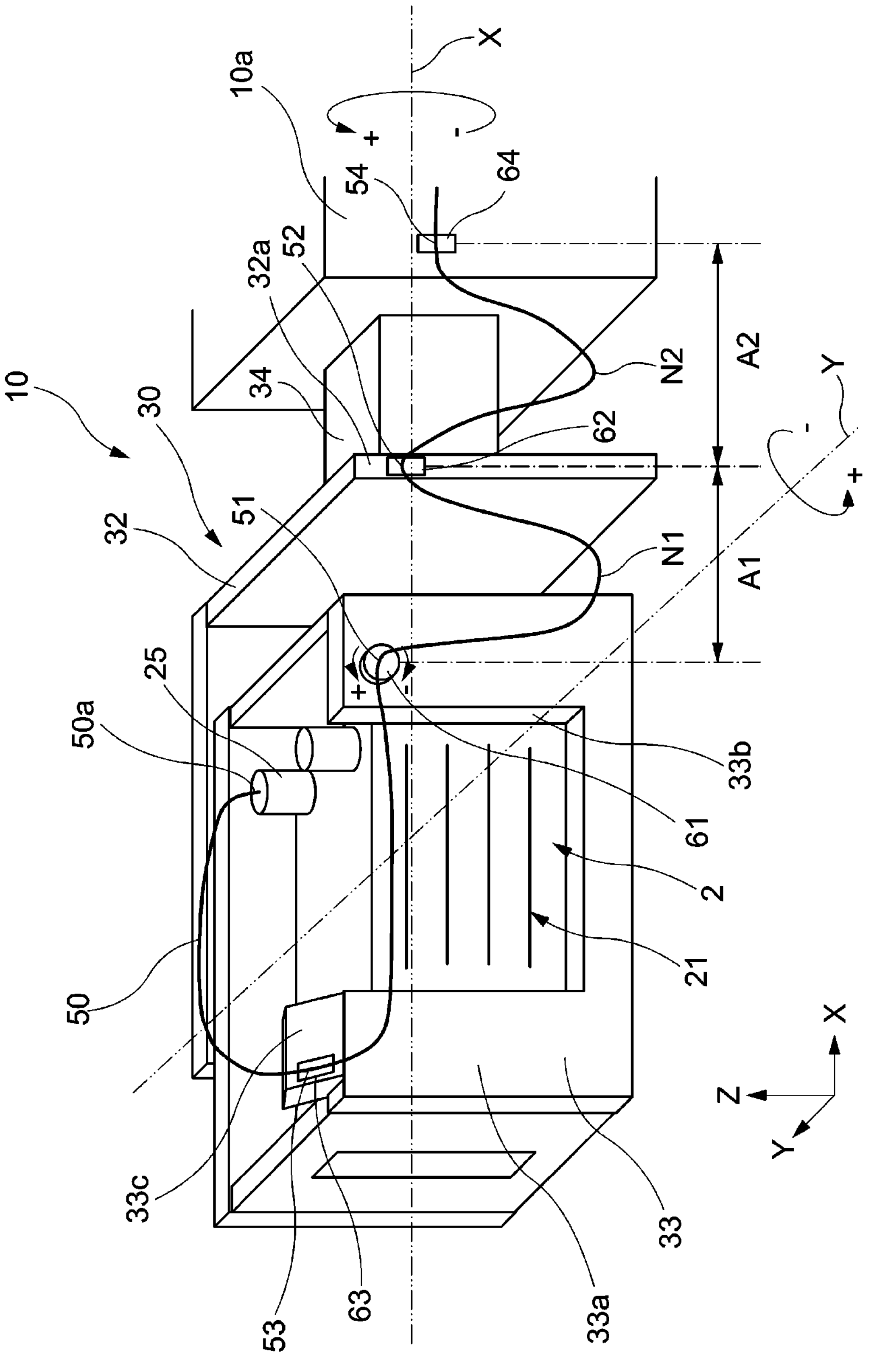
FIG. 4 is a diagram showing a drive mechanism of a cell culture device.
Figure 5:
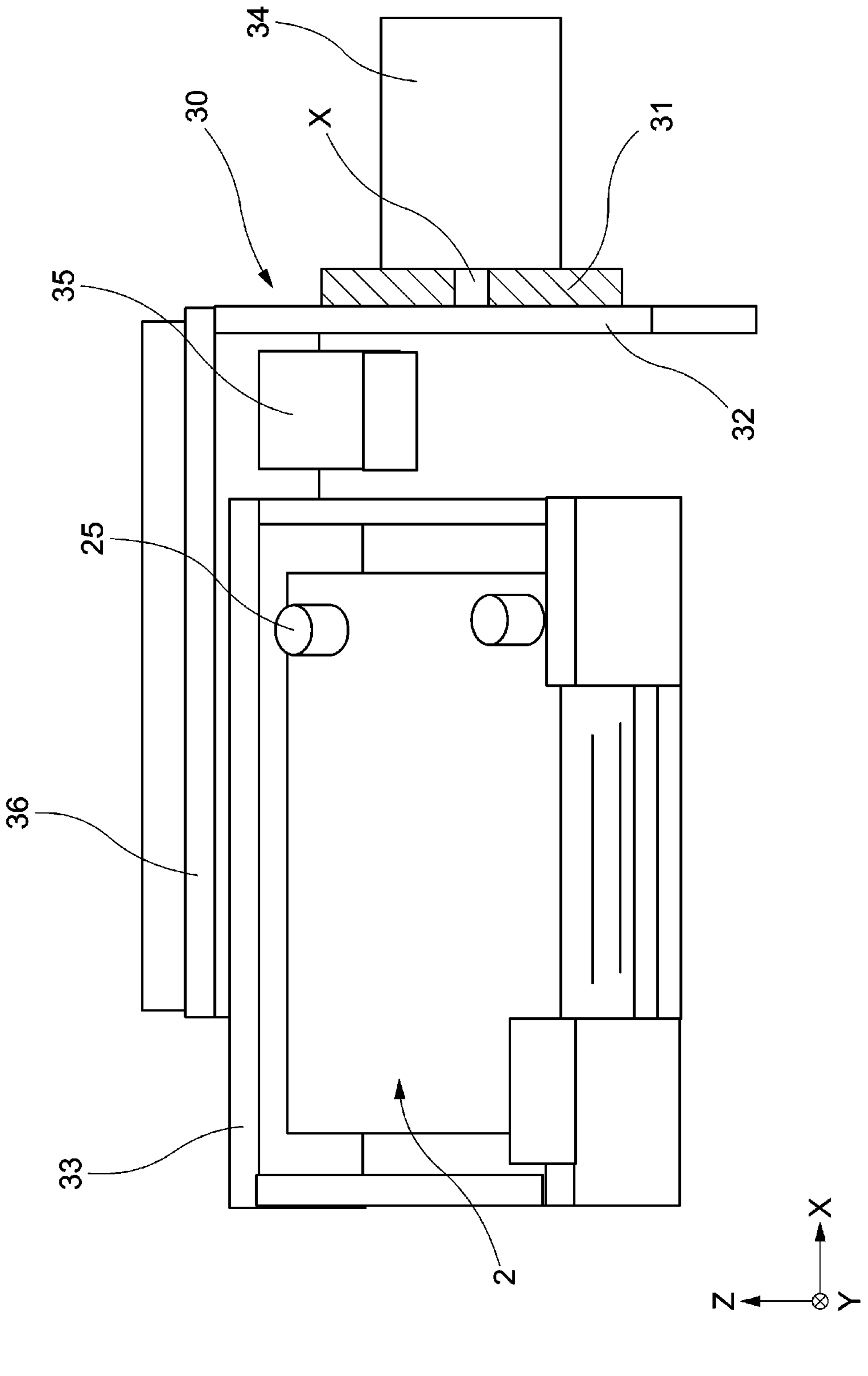
FIG. 5 is a diagram showing the drive mechanism of the cell culture device.
Figure 6:
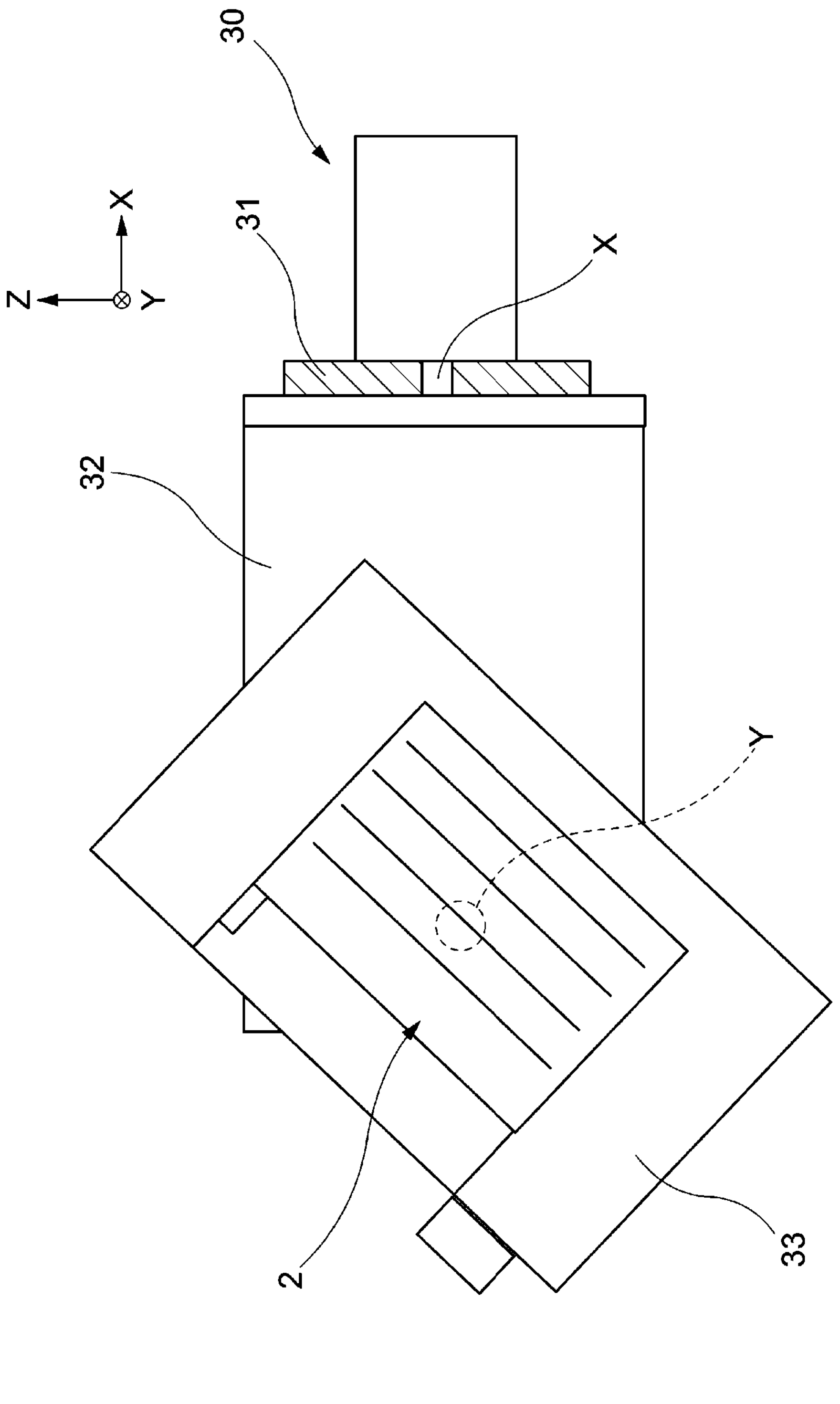
FIG. 6 is a diagram showing the drive mechanism of the cell culture device.

As shown in FIGS. 4 to 6, the cell culture device 10 includes a drive mechanism 30 for changing the posture of the cell culture container 2. In FIG. 4, there is shown the liquid supply/drainage tube 50 that serves as a liquid tube for both supplying a liquid to the cell culture container 2 and draining the liquid from the cell culture container 2. In FIGS. 5 and 6, illustration of the liquid supply/drainage tube 50 is omitted.

The drive mechanism 30 includes a base 31, a rotary table 32 attached to the base 31 and capable of rotating around a first axis X, a container holding member 33 attached to the rotary table 32 and capable of rotating around a second axis Y, a first drive part 34 configured to rotationally drive the rotary table 32 around the first axis X, a second drive part 35 configured to rotationally drive the container holding member 33 around the second axis Y, and the controller C as a control part configured to control the drive parts 34 and 35.

As shown in FIG. 4, the counterclockwise rotation around the first axis X is assumed to be rotation in a positive direction (+), and the clockwise rotation around the first axis X is assumed to be rotation in a negative direction (−). Similarly, the counterclockwise rotation around the second axis Y is assumed to be rotation in a positive direction (+), and the clockwise rotation around the second axis Y is assumed to be rotation in a negative direction (−).

The first drive part 34 is located in a direction extending along the first axis X from the cell culture container 2, and the second drive part 35 is disposed in the vicinity of the first drive part 34 and is connected to the second axis Y via a transmission mechanism 36 including a belt, a chain and the like, which transmit power along the first axis X.

That is, when only the first drive part 34 is driven, as shown in FIG. 5, the rotary table 32, the container holding member 33, and the cell culture container 2 are rotated around the first axis X. When only the second drive part 35 is driven, as shown in FIG. 6, the rotary table 32 is not rotated and the container holding member 33 and the cell culture container 2 are rotated around the second axis Y. When the first drive part 34 and the second drive part 35 are driven at the same time, the rotary table 32, the container holding member 33, and the cell culture container 2 are rotated around the first axis X as shown in FIG. 5, and the container holding member 33 and the cell culture container 2 are further rotated with respect to the rotary table 32 about the second axis Y as shown in FIG. 6. The drive mechanism 30 may control the posture of the cell culture container 2 through an open control or may feedback-control the posture of the cell culture container 2 by providing a sensor or the like for detecting the posture of the shelf surface 21*b*.

On the outer peripheral surface of the cell culture container 2, there is provided the liquid supply/drainage port 25 that serves as both a supply liquid port and a drainage liquid port. The liquid supply/drainage tube 50 connected to the liquid storage part 1 and the cell recovery part 3 is connected to the liquid supply/drainage port 25. The liquid supply/drainage tube 50 is used for supplying a reagent into the cell culture container 2 and draining the reagent from the cell culture container 2.

FIG. 4 shows a state in which the shelf surface 21*b* of the cell culture container 2 is arranged in a horizontal culture posture. In that state, the container holding member 33 has a substantially rectangular parallelepiped shape with an open upper surface. A substantially rectangular opening 33*b* is formed in a front portion 33*a* of the container holding member 33. In the state of FIG. 4, the rotary table 32 is disposed so as to face a right-hand side surface portion and a back surface portion of the container holding member 33.

A first predetermined portion 51 of the liquid supply/drainage tube 50, which is spaced apart from a connection portion 50*a* connected to the liquid supply/drainage port 25 by a predetermined length along a longitudinal direction of the liquid supply/drainage tube 50, is positioned on the container holding member 33 by a first positioning member 61. The first positioning member 61 that holds the first predetermined portion 51 is disposed on a right-hand side of the opening 33*b* in the vicinity of the upper end of the front portion 33*a* of the container holding member 33.

A second predetermined portion 52 of the liquid supply/drainage tube 50, which is further spaced apart from the connection portion 50*a* connected to the liquid supply/drainage port 25 than the first predetermined portion 51, is positioned on the rotary table 32 by a second positioning member 62. The second positioning member 62 is disposed on a front portion 32*a* of a plate-shaped member of the rotary table 32 facing the right-hand side surface portion of the container holding member 33.

A third predetermined portion 53 of the liquid supply/drainage tube 50, which is closer to the connection portion 50*a* than the first predetermined portion 51, is positioned on the container holding member 33 by a third positioning member 63. The third positioning member 63 is positioned on an attachment portion 33*c* protruding upward from a left-hand side of the opening 33*b* at the upper end of the front portion 33*a* of the container holding member 33. Therefore, the first predetermined portion 51 and the third predetermined portion 53 of the liquid supply/drainage tube 50 are positioned on the same plane with respect to the container holding member 33.

A fourth predetermined portion 54 of the liquid supply/drainage tube 50, which is further spaced apart from the connection portion 50*a* than the second predetermined portion 52, is fixed to a housing 10*a* of the cell culture device 10 by a fourth positioning member 64 so as not to move. That is, the first predetermined portion 51, the second predetermined portion 52, the third predetermined portion 53, and the fourth predetermined portion 54 are spaced apart from one another in the longitudinal direction of the liquid supply/drainage tube 50.

The first positioning member 61 is rotatably attached to the front portion 33*a* of the container holding member 33. Referring to FIG. 4, the counterclockwise rotation of the first positioning member 61 is assumed to be rotation in a positive direction (+), and the clockwise rotation of the first positioning member 61 is assumed to be rotation in a negative direction (−). Therefore, the first predetermined portion 51 of the liquid supply/drainage tube 50 positioned by the first positioning member 61 can rotate along the surface of the container holding member 33 together with the first positioning member 61. That is, as shown in FIG. 4, the first predetermined portion 51 of the liquid supply/drainage tube 50 can rotate 360 degrees along the surface of the front portion 33*a* of the container holding member 33.

On the other hand, the second positioning member 62 is fixed so as not to move with respect to the front portion 32*a* of the rotary table 32. Therefore, the second predetermined portion 52 of the liquid supply/drainage tube 50 positioned by the second positioning member 62 is immovable on the front portion 32*a* of the rotary table 32. That is, as shown in FIG. 4, the second predetermined portion 52 of the liquid supply/drainage tube 50 is fixed to the rotary table 32 in a state in which the second predetermined portion 52 is disposed substantially parallel to a thickness direction of the front portion 32*a* of the rotary table 32.

Similarly, the third positioning member 63 is fixed so as not to move with respect to the attachment portion 33*c* of the container holding member 33. Therefore, the third predetermined portion 53 of the liquid supply/drainage tube 50 positioned by the third positioning member 63 is immovable on the surface of the attachment portion 33*c* of the container holding member 33. That is, as shown in FIG. 4, the third predetermined portion 53 of the liquid supply/drainage tube 50 is fixed to the container holding member 33 in a state in which the third predetermined portion 53 is disposed substantially parallel to the attachment portion 33*c* of the container holding member 33 in the vertical direction.

In the cell culture device 10 of the present embodiment, when the reagent is supplied to the cell culture container 2 or when the reagent is drained from the cell culture container 2, the rotary table 32 and/or the container holding member 33 is rotationally driven in a state in which the liquid supply/drainage tube 50 is connected to the liquid supply/drainage port 25. Therefore, the liquid supply/drainage tube 50 is loosened to have an extra length in a section A1 between the first positioning member 61 attached to the container holding member 33 and the second positioning member 62 attached to the rotary table 32 and in a section A2 between the second positioning member 62 attached to the rotary table 32 and the fourth positioning member 64 attached to the surface of the housing of the cell culture device 10.

That is, an extra length portion N1 is formed between the first predetermined portion 51 and the second predetermined portion 52 of the liquid supply/drainage tube 50, and an extra length portion N2 is formed between the second predetermined portion 52 and the fourth predetermined portion 54 of the liquid supply/drainage tube 50. As a result, even when the rotary table 32 and/or the container holding member 33 is rotationally driven, the liquid supply/drainage tube 50 is pulled so as not to restrict the rotation of the rotary table 32 and/or the container holding member 33.

Figure 7A:
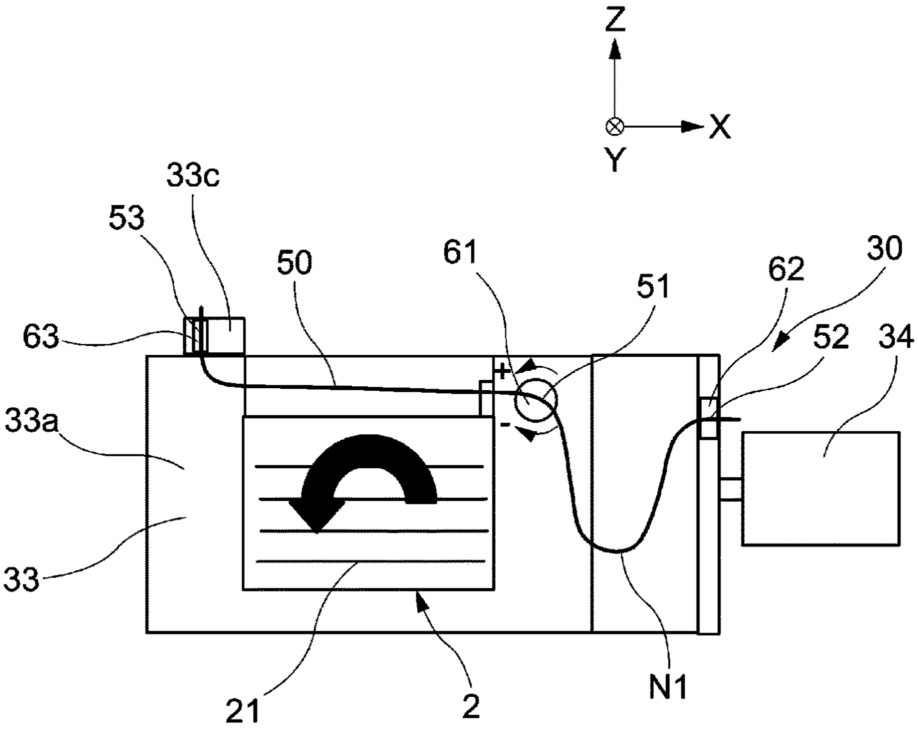
FIGS. 7A and 7B are diagrams showing a state change of a liquid supply/drainage tube when a container holding member is rotationally driven around a second axis Y.
Figure 7B:
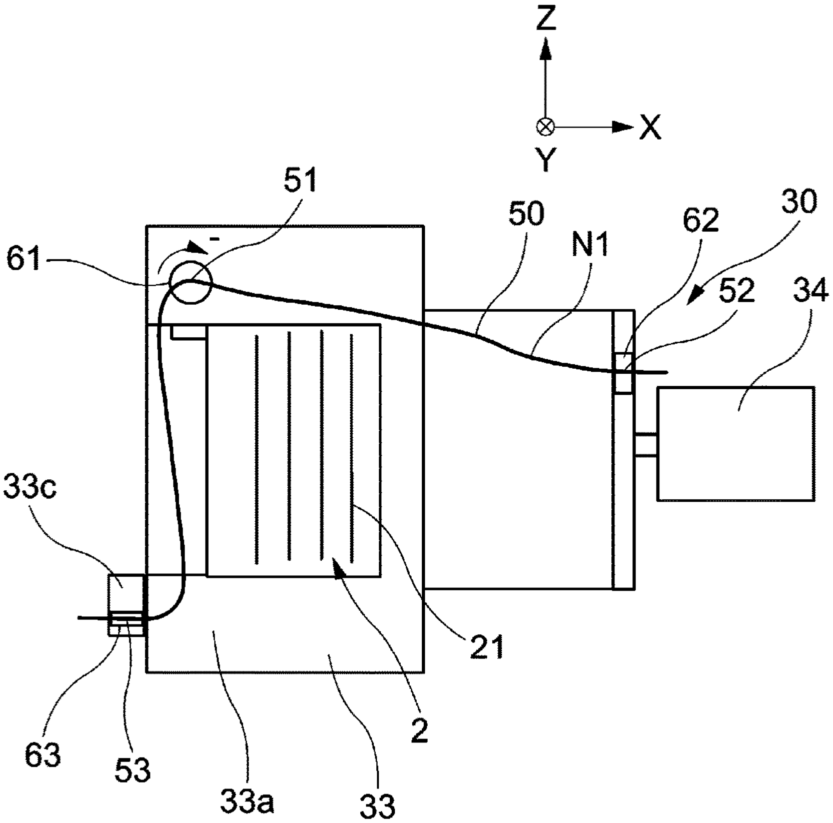

FIG. 7A shows a state in which the shelf surface 21*b* of the cell culture container 2 is arranged in the horizontal culture posture. In this state, when the container holding member 33 is rotationally driven by the second drive part 35 around the second axis Y by +90 degrees, as shown in FIG. 7B, the first predetermined portion 51 and the third predetermined portion 53 of the liquid supply/drainage tube 50 are positioned on the container holding member 33 by the first positioning member 61 and the third positioning member 63, respectively. Therefore, the first predetermined portion 51 and the third predetermined portion 53 of the liquid supply/drainage tube 50 are moved together with the rotation of the container holding member 33 in a state in which a length between the first predetermined portion 51 and the third predetermined portion 53 of the liquid supply/drainage tube 50 is maintained substantially constant.

Further, the second predetermined portion 52 of the liquid supply/drainage tube 50 is positioned on the rotary table 32 by the second positioning member 62. As the container holding member 33 rotates, a distance between the first positioning member 61 and the second positioning member 62 increases. Therefore, a slack portion of the extra length portion N1 formed between the first predetermined portion 51 and the second predetermined portion 52 of the liquid supply/drainage tube 50 is changed to become small.

At this time, a force pulling the first predetermined portion 51 toward the second predetermined portion 52 acts on the first predetermined portion 51 of the liquid supply/drainage tube 50 positioned on the container holding member 33 by the first positioning member 61. Therefore, the first predetermined portion 51 of the liquid supply/drainage tube 50 rotates in the negative direction (−) along the surface of the container holding member 33.

Figure 8A:
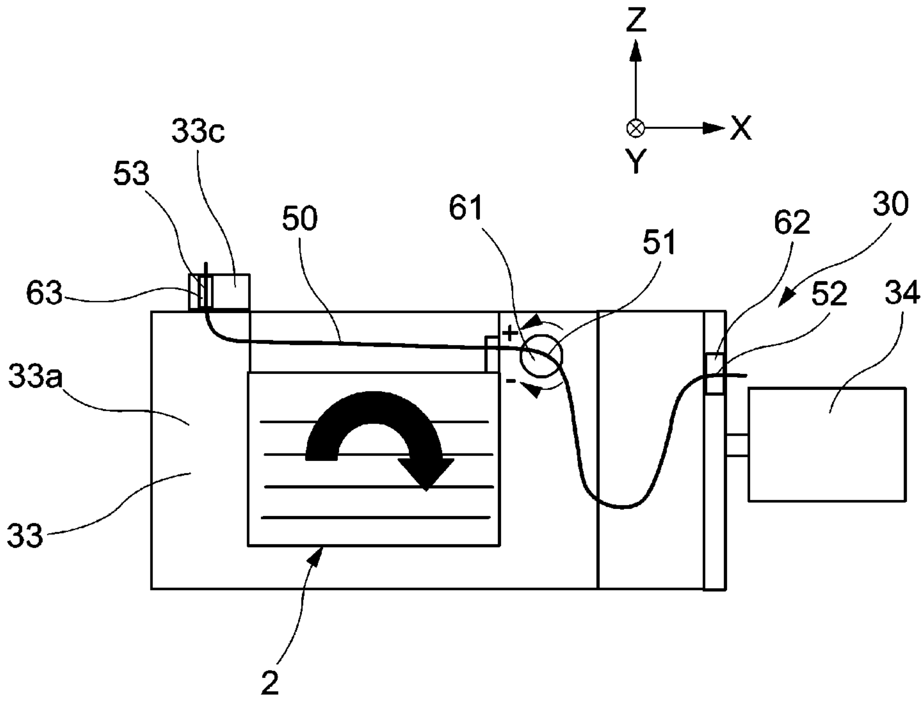
FIGS. 8A and 8B are diagrams showing a state change of the liquid supply/drainage tube when the container holding member is rotationally driven around the second axis Y.
Figure 8B:
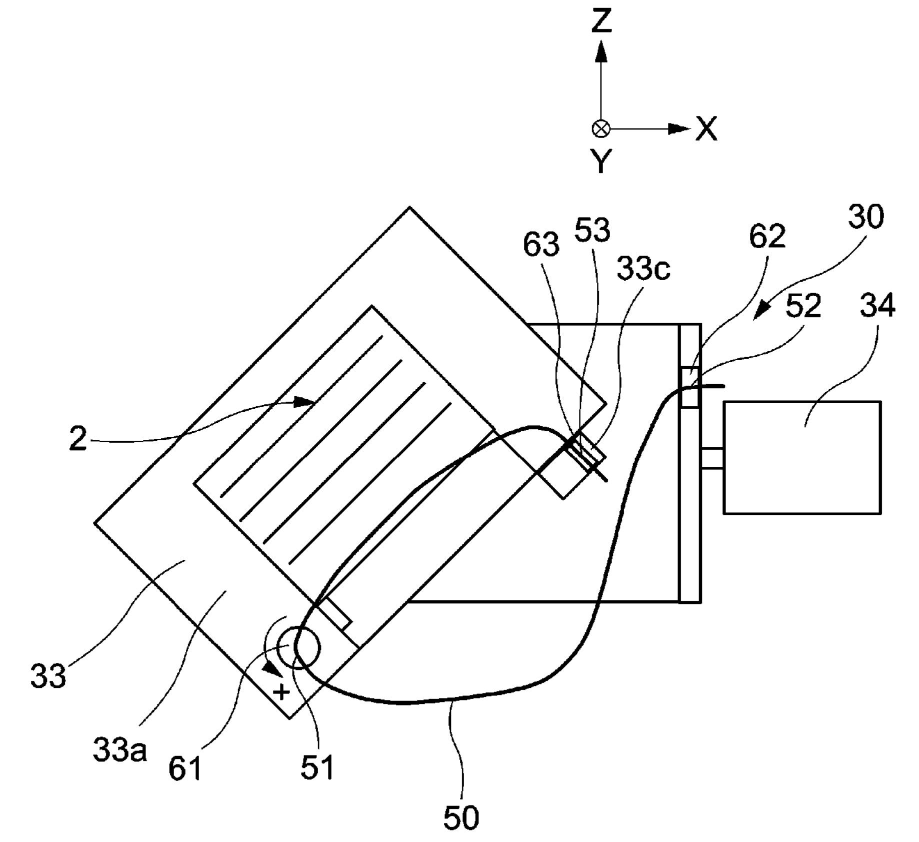

In addition, FIG. 8A shows a state in which the shelf surface 21*b* of the cell culture container 2 is arranged in the horizontal culture posture. In this state, when the container holding member 33 is rotationally driven by the second drive part 35 around the second axis Y by −135 degrees, as shown in FIG. 8B, the first predetermined portion 51 and the third predetermined portion 53 of the liquid supply/drainage tube 50 are positioned on the container holding member 33 by the first positioning member 61 and the third positioning member 63, respectively. Therefore, the first predetermined portion 51 and the third predetermined portion 53 of the liquid supply/drainage tube 50 are moved together with the rotation of the container holding member 33 in a state in which the length between the first predetermined portion 51 and the third predetermined portion 53 of the liquid supply/drainage tube 50 is kept substantially constant.

Further, the second predetermined portion 52 of the liquid supply/drainage tube 50 is positioned on the rotary table 32 by the second positioning member 62. As the container holding member 33 rotates, the distance between the first positioning member 61 and the second positioning member 62 increases. Therefore, the slack portion of the extra length portion N1 formed between the first predetermined portion 51 and the second predetermined portion 52 of the liquid supply/drainage tube 50 is changed to become small.

At this time, a force pulling the first predetermined portion 51 toward the second predetermined portion 52 acts on the first predetermined portion 51 of the liquid supply/drainage tube 50 positioned on the container holding member 33 by the first positioning member 61. Therefore, the first predetermined portion 51 of the liquid supply/drainage tube 50 rotates in the positive direction (+) along the surface of the container holding member 33.

When rotating the cell culture container 2, it is necessary to rotate the cell culture container 2 at such a speed as not to shake the medium and not to give excessive stimulation to the cells. Furthermore, it is necessary to evenly supply the liquid to the respective shelves 21. Therefore, a posture control is performed by the following procedure.

(Liquid Supply Operation)

Figure 9A:
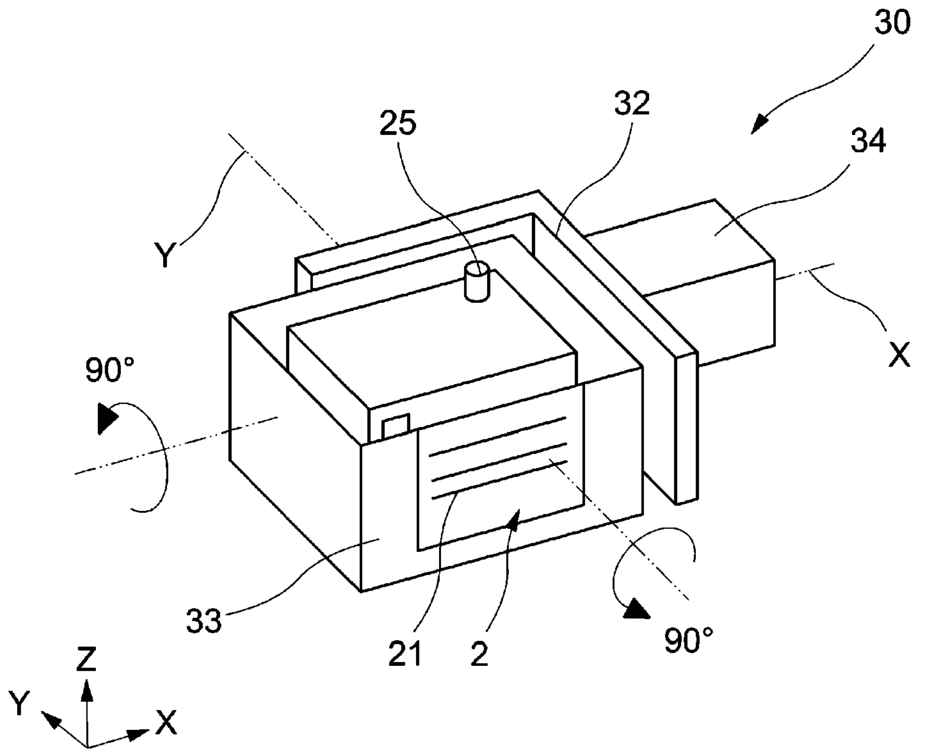
FIGS. 9A and 9B are diagrams illustrating a liquid supply operation.
Figure 9B:
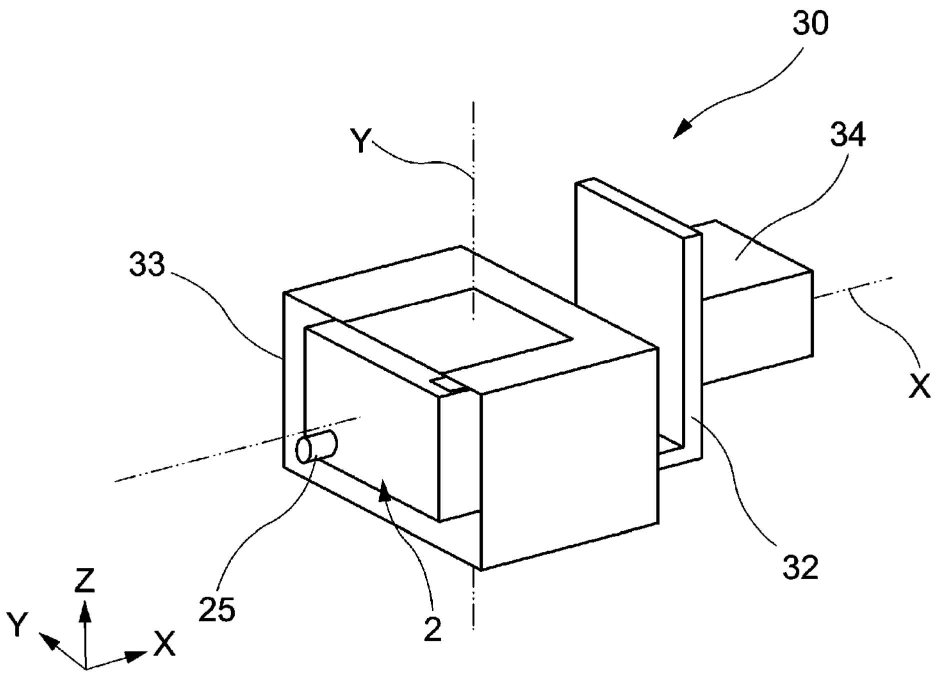

In a state in which the shelf surface 21*b* of the cell culture container 2 shown in FIG. 9A is arranged in the horizontal culture posture, the controller C for driving the drive parts 34 and 35 drives the first drive part 34 to rotate the container holding member 33 and the cell culture container 2 around the first axis X by +90 degrees so that the liquid supply/drainage port 25 is located on the bottom side as shown in FIG. 9B, and further drives the second drive part 35 to rotate the cell culture container 2 around the second axis Y by +90 degrees, whereby each shelf surface 21*b* is erected to take a liquid supply posture.

Then, after supplying the liquid to the horizontally oriented liquid supply/drainage port 25 and allowing the liquid to evenly enter each shelf space, the first drive part 34 is driven to rotate the cell culture container 2 around the first axis X by −90 degrees. At this time, when the liquid supply/drainage port 25 becomes higher than the liquid level, the second drive part 35 is also driven to rotate the cell culture container 2 around the second axis Y by −90 degrees, whereby each shelf surface 21*b* is brought into the horizontal culture posture to distribute the liquid substantially evenly on each shelf surface 21*b*.

(Liquid Drainage Operation)

Figure 10A:
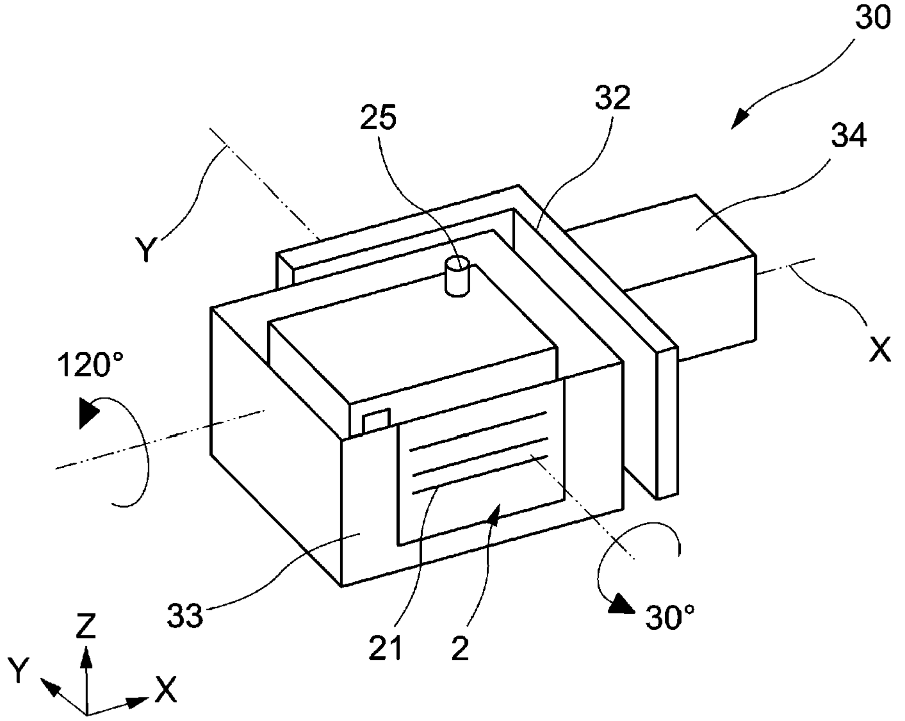
FIGS. 10A and 10B are diagrams illustrating a liquid drainage operation.
Figure 10B:
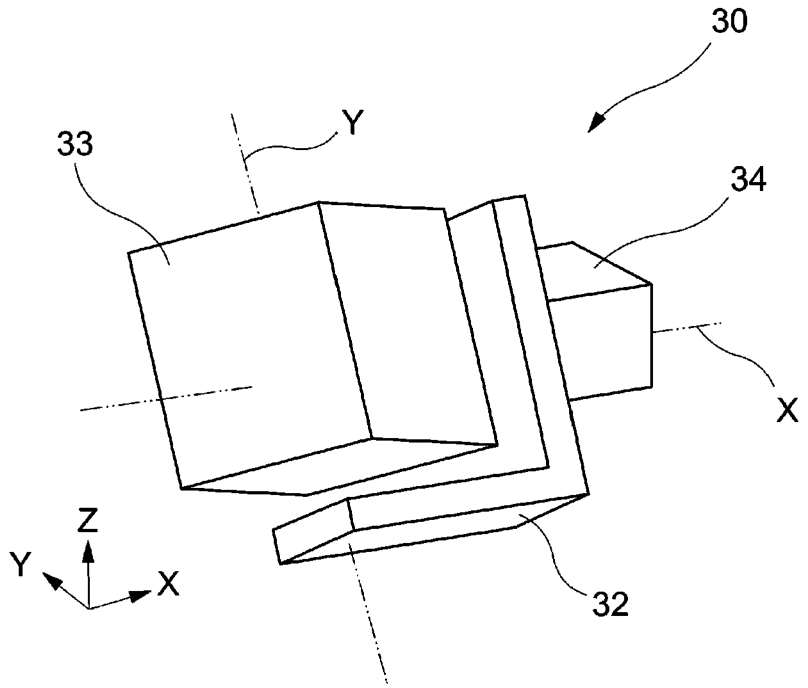

In a liquid drainage operation for draining the reagent, in a state in which the shelf surface 21*b* of the cell culture container 2 is arranged in the horizontal culture posture as shown in FIG. 10A, first, the rotary table 32 and the container holding member 33 are rotated around the first axis X by +120 degrees, and the container holding member 33 is rotated around the second axis Y by +30 degrees. Then, as shown in FIG. 10B, the liquid supply/drainage port 25 faces downward, and the liquid in each shelf space comes out to the communication portion 21*c* to reach the liquid supply/drainage port 25 (first liquid drainage posture). In the present embodiment, the liquid drainage operation for draining the reagent includes a liquid drainage operation for draining a liquid such as a culture solution or the like.

Figure 11A:
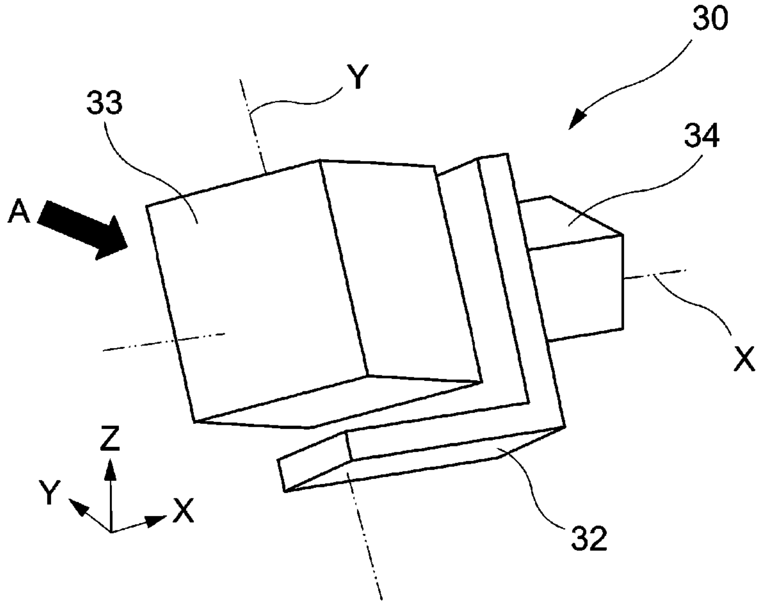
FIGS. 11A and 11B are diagrams illustrating a first drainage posture in the liquid drainage operation.
Figure 11B:
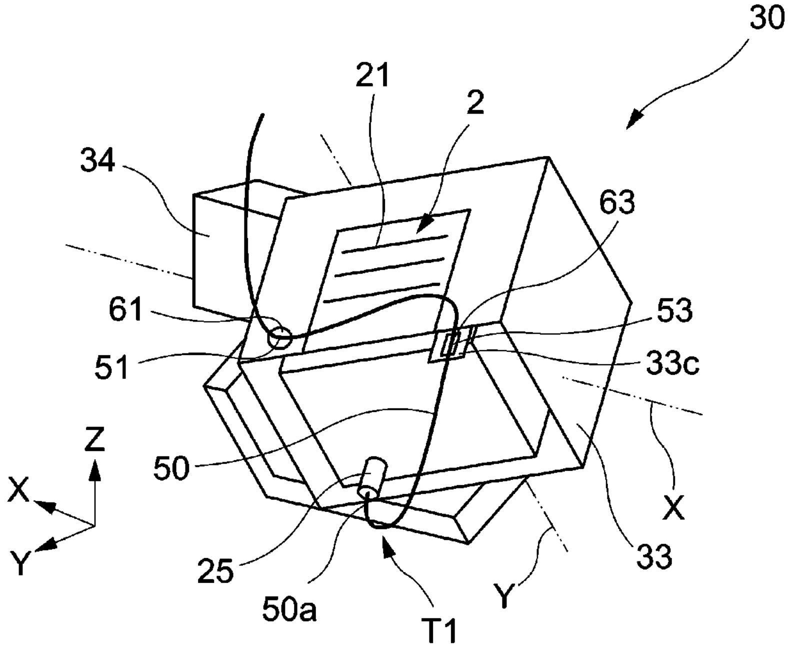

FIGS. 11A and 11B are diagrams for explaining the first liquid drainage posture. FIG. 11B is a diagram seen from the direction A in FIG. 11A. In the first liquid drainage posture shown in FIGS. 11A and 11B, when a diameter of the liquid supply/drainage tube 50 is large and the liquid supply/drainage tube 50 has an ascending gradient toward a downstream side, the liquid cannot move upward completely and remains in a region T1 which is the lowest point in FIG. 11B. In this case, when a new reagent is supplied into the cell culture container, the used liquid is mixed with the new reagent, which may affect growth of cells. For example, in a process of supplying a peeling liquid, when a residual liquid remains in the liquid supply/drainage tube 50 after draining the medium used in the previous process, the peeling liquid is diluted, and the peeling may not be performed properly.

As a method of preventing a liquid from remaining in the liquid supply/drainage tube 50, it is conceivable to reduce the diameter of the liquid supply/drainage tube 50. However, this may affect the cells due to a long liquid feeding time and a long cell floating time. When a flow rate is increased to shorten the liquid feeding time, an excessive shearing force may act on the cells and may affect the cells.

Therefore, in the cell culture device of the present embodiment, by appropriately controlling the drive mechanism 30, the rotary table 32 and the container holding member 33 are rotationally driven so that the liquid does not remain in the liquid supply/drainage tube 50 at the time of liquid drainage.

Figure 12A:
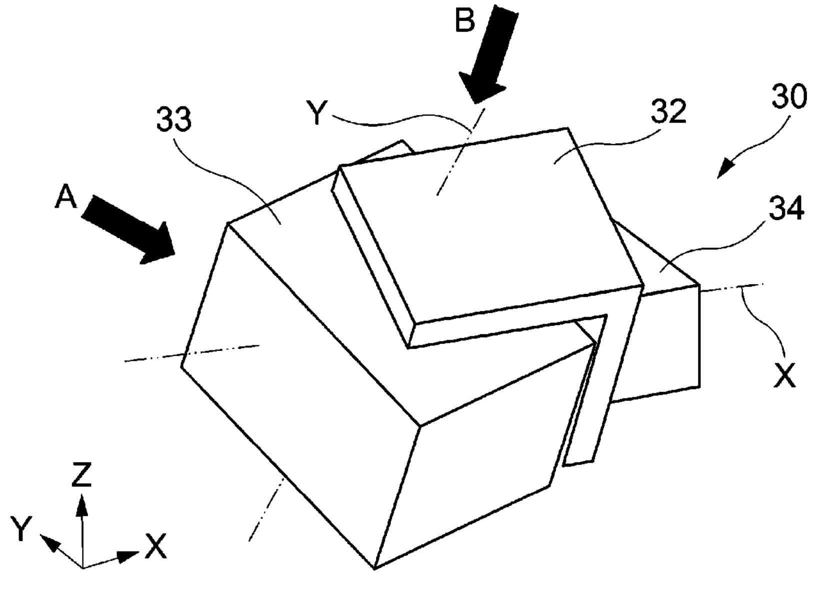
FIGS. 12A, 12B and 12C are diagrams illustrating a second drainage posture in the liquid drainage operation.
Figure 12B:
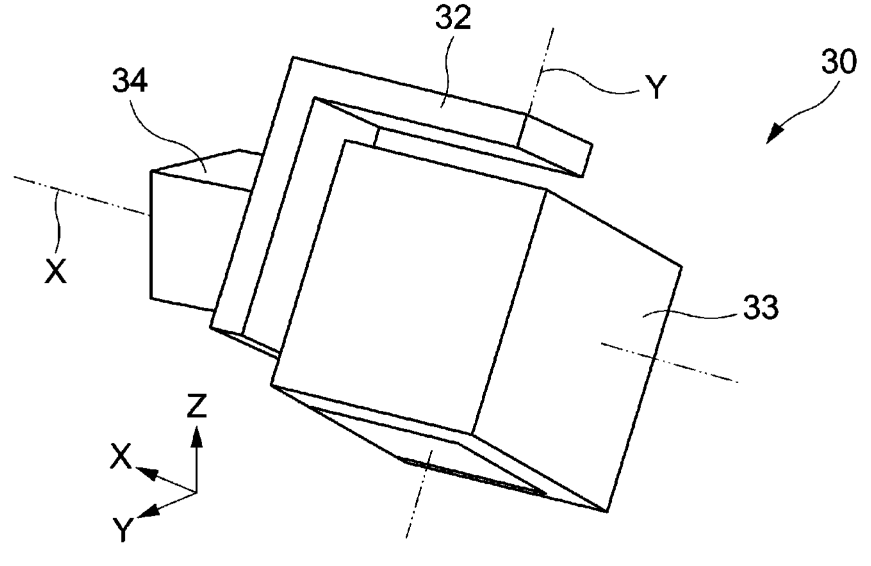
Figure 12C:
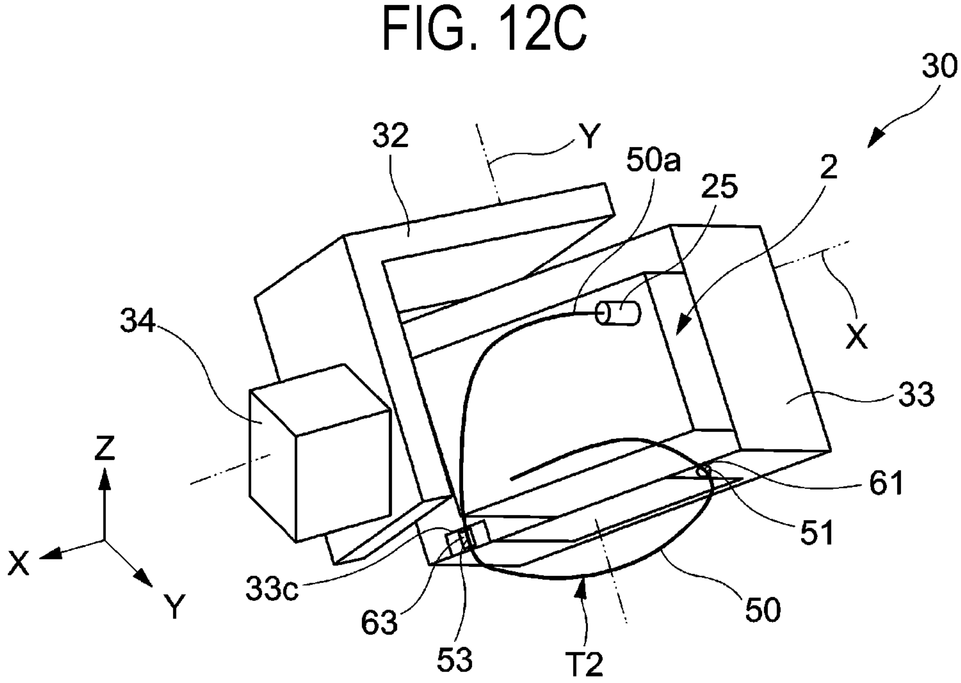

In the first liquid drainage posture of FIGS. 11A and 11B, when the rotary table 32 and the container holding member 33 are rotated around the first axis X by −220 degrees and the container holding member 33 is rotated around the second axis Y by −150 degrees, the liquid supply/drainage port 25 is moved upward (second liquid drainage posture). FIGS. 12A to 12C are diagrams for explaining the second liquid drainage posture. FIG. 12B is a diagram seen from the direction A in FIG. 12A. FIG. 12C is a diagram seen from the direction B in FIG. 12A. Therefore, the region T1 which was the lowest point in FIG. 11B moves upward, and the liquid remaining in the region T1 moves to the downstream side of the liquid supply/drainage tube 50 (in a direction away from the connection portion 50*a* of the liquid supply/drainage tube 50) and moves to a region T2 which is the lowest point in FIG. 12C.

Figure 13A:
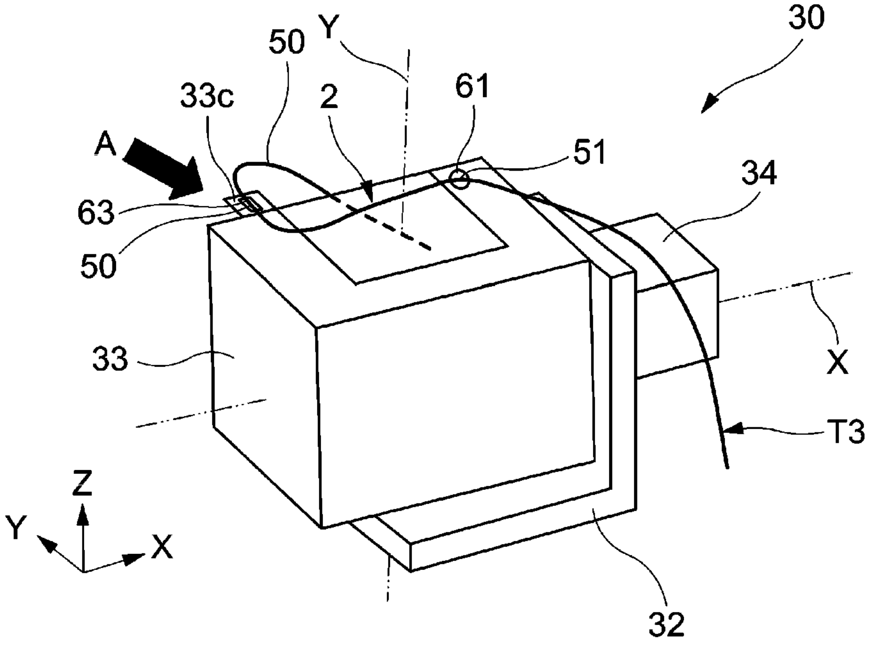
FIGS. 13A and 13B are diagrams illustrating a third drainage posture in the liquid drainage operation.
Figure 13B:
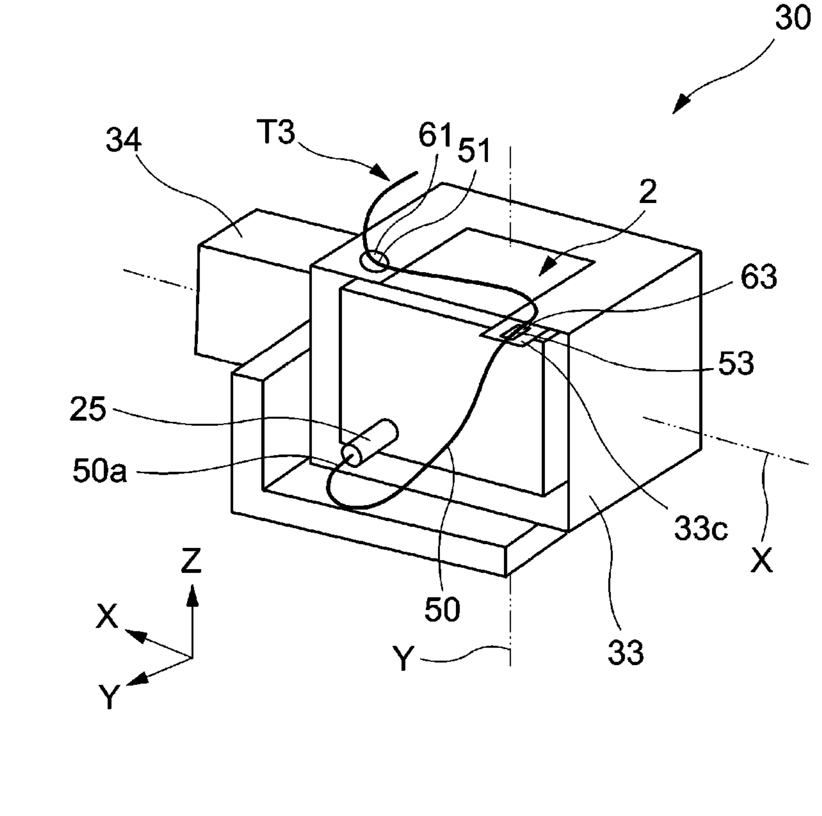

In the second liquid drainage posture of FIGS. 12A to 12C, when the rotary table 32 and the container holding member 33 are rotated around the first axis X by +190 degrees and the container holding member 33 is rotated around the second axis Y by +120 degrees, the liquid supply/drainage port 25 moves downward (third liquid drainage posture). FIGS. 13A and 13B are diagrams for explaining the third liquid drainage posture. FIG. 13B is a diagram seen from the direction A in FIG. 13A. Therefore, the region T2, which was the lowest point in FIG. 12C, moves upward, and the liquid in the region T2 moves toward a region T3 on the downstream side of the liquid supply/drainage tube 50, whereby the entire liquid is removed from the inside of the liquid supply/drainage tube 50.

Accordingly, since the liquid supply/drainage tube 50 does not have an ascending gradient toward the downstream side when the liquid moves toward the downstream side of the liquid supply/drainage tube 50, the liquid always flows toward the lowest point. This makes it possible to reduce the amount of liquid remaining in the liquid supply/drainage tube 50. During the liquid drainage operation, a pump is continuously rotated to prevent the liquid from flowing back and to allow the liquid to flow toward the downstream side of the liquid supply/drainage tube 50. After the liquid drainage is completed, the process returns to the liquid supply posture shown in FIG. 9B for a subsequent liquid supply.

As described above, the cell culture device 10 of the present embodiment includes: the base 31; the rotary table 32 attached to the base 31 and capable of rotating around the first axis X; the container holding member 33 attached to the rotary table 32, capable of rotating around the second axis Y, and configured to hold the cell culture container 2; and the drive mechanism 30 configured to rotationally drive the rotary table 32 around the first axis X and to rotationally drive the container holding member 33 around the second axis Y. The liquid supply/drainage port 25 to which the liquid supply/drainage tube 50 is connected is arranged on the outer peripheral surface of the cell culture container 2. The first predetermined portion 51 of the liquid supply/drainage tube 50, which is spaced apart by a predetermined length from the connection portion 50*a* connected to the liquid supply/drainage port 25, is positioned on the container holding member 33 by the first positioning member 61, and the second predetermined portion 52 of the liquid supply/drainage tube 50, which is further spaced apart from the connection portion 50*a* than the first predetermined portion 51, is positioned on the rotary table 32 by the second positioning member 62. The first positioning member 61 is rotatably attached to the container holding member 33.

As a result, by rotatably attaching the first positioning member 61 for positioning the first predetermined portion 51 of the liquid supply/drainage tube 50 to the container holding member 33, it is possible to eliminate an extra length portion formed between the first predetermined portion 51 and the second predetermined portion 52 of the liquid supply/drainage tube 50. Therefore, in the case of supplying a reagent into the cell culture container 2 or draining the reagent from the cell culture container 2, it is possible to prevent the extra length portion of the liquid supply/drainage tube 50 connected to the liquid supply/drainage port 25 from becoming too long, so that the culture can be continued properly even when the rotary table 32 and/or the container holding member 33 is rotationally driven in a state in which the liquid supply/drainage tube 50 is connected to the liquid supply/drainage port 25.

In the cell culture device 10 of the present embodiment, the third predetermined portion 53 of the liquid supply/drainage tube 50, which is closer to the connection portion 50*a* than the first predetermined portion 51, is positioned on the container holding member 33 by the third positioning member 63.

As a result, when the rotary table 32 and/or the container holding member 33 is rotationally driven in a state in which the liquid supply/drainage tube 50 is connected to the liquid supply/drainage port 25, the direction of the first predetermined portion 51 of the liquid supply/drainage tube 50, which is rotatably positioned on the container holding member 33 by the first positioning member 61, is easily changed. Therefore, it is possible to easily eliminate the extra length portion formed between the first predetermined portion 51 and the second predetermined portion 52 of the liquid supply/drainage tube 50.

In the cell culture device 10 of the present embodiment, the first predetermined portion 51 and the third predetermined portion 53 are positioned on the same plane with respect to the container holding member 33.

As a result, the direction of the first predetermined portion 51 of the liquid supply/drainage tube 50, which is rotatably positioned on the container holding member 33 by the first positioning member 61, is easily changed. Therefore, it is possible to further eliminate the extra length portion formed between the first predetermined portion 51 and the second predetermined portion 52 of the liquid supply/drainage tube 50.

In the cell culture device 10 of the present embodiment, the drive mechanism 30 is configured to rotationally drive the rotary table 32 and the container holding member 33 so that in the liquid drainage operation for draining a reagent from the cell culture container 2, the reagent flowing out from the liquid supply/drainage port 25 into the liquid supply/drainage tube 50 flows in the liquid supply/drainage tube 50 in a direction away from the liquid supply/drainage port 25 under a gravitational force acting on the reagent.

As a result, it is possible to prevent the reagent from remaining in the liquid supply/drainage tube 50 after the reagent is drained from the cell culture container 2.

Although the embodiment of the present disclosure has been described above, specific configurations of individual components are not limited to the above-described embodiment.

For example, in the above-described embodiment, the first predetermined portion 51 is positioned on the right-hand side of the opening 33*b* near the upper end of the front portion 33*a* of the container holding member 33, and the second predetermined portion 52 is positioned on the front portion 32*a* of the plate-shaped member of the rotary table 32 facing the right-hand side surface portion of the container holding member 33. However, the present disclosure is not limited thereto. The location where the first predetermined portion 51 is positioned on the container holding member 33 and the location where the second predetermined portion 52 is positioned on the rotary table 32 are arbitrary.

In the above-described embodiment, the third predetermined portion 53 of the liquid supply/drainage tube 50, which is closer to the connection portion 50*a* than the first predetermined portion 51, is positioned on the container holding member 33 by the third positioning member 63. However, the present disclosure is not limited thereto. The portion between the connection portion 50*a* and the first predetermined portion 51 of the liquid supply/drainage tube 50 does not have to be positioned on the container holding member 33. Further, when the portion between the connection portion 50*a* and the first predetermined portion 51 of the liquid supply/drainage tube 50 is positioned on the container holding member 33, the number of positioning locations is arbitrary.

In the above-described embodiment, the first predetermined portion 51 of the liquid supply/drainage tube 50 is attached to the container holding member 33 and is capable of rotating by 360 degrees. However, the present disclosure is not limited thereto. The range within which the first predetermined portion 51 can rotate with respect to the container holding member 33 is arbitrary.

In the above-described embodiment, the second predetermined portion 52 of the liquid supply/drainage tube 50 is fixed so as not to move with respect to the rotary table 32. However, the second predetermined portion 52 may be rotatably attached to the rotary table 32. Similarly, in the above-described embodiment, the third predetermined portion 53 of the liquid supply/drainage tube 50 is fixed so as not to move with respect to the container holding member 33. However, the third predetermined portion 53 may be rotatably attached with respect to the container holding member 33. In the above-described embodiment, not only the first positioning member 61 but also any of the first positioning member 61, the second positioning member 62, and the third positioning member 63 may be rotatable with respect to the rotary table 32 or the container holding member 33.

In the above-described embodiment, the first predetermined portion 51 and the third predetermined portion 53 are positioned on the same plane with respect to the container holding member 33. However, the present disclosure is not limited thereto. The first predetermined portion 51 and the third predetermined portion 53 may be positioned on different planes.

In the above-described embodiment, the liquid supply/drainage port 25 and the liquid supply/drainage tube 50 are used for both liquid supply and liquid drainage. However, the present disclosure is not limited thereto. Different liquid ports or liquid tubes may be used for the liquid supply and the liquid drainage, respectively, and the liquid supply route and the liquid drainage route may be separated.

In the above-described embodiment, in the liquid drainage operation for draining the reagent from the cell culture container 2, the rotary table 32 and the container holding member 33 are rotationally driven so that the posture thereof is changed in the order of the first liquid drainage posture, the second liquid drainage posture, and the third liquid drainage posture. However, the present disclosure is not limited thereto. The order of changing the posture of the rotary table 32 and the container holding member 33 may be an order other than the aforementioned order as long as, in the liquid drainage operation for draining the reagent from the cell culture container 2, the reagent flowing out from the liquid supply/drainage port 25 into the liquid supply/drainage tube 50 flows in the liquid supply/drainage tube 50 in the direction away from the liquid supply/drainage port 25 under the gravitational force acting on the reagent.

Even when the first predetermined portion 51 of the liquid supply/drainage tube 50 is fixed to the container holding member 33 so as not to rotate, the rotary table 32 and the container holding member 33 can be rotationally driven so that in the liquid drainage operation, the reagent flowing out from the liquid supply/drainage port 25 into the liquid supply/drainage tube 50 flows in the liquid supply/drainage tube 50 in the direction away from the liquid supply/drainage port 25 under the gravitational force acting on the reagent.

In the above-described embodiment, the cell culture container 2 having a multi-stage shelf structure is used. However, a cell culture container 2 having a structure other than the multi-stage shelf structure may be used. In the above-described embodiment, the liquid supply/drainage tube 50 is not limited to the tube through which the liquid such as the reagent or the culture solution flows, and may be a tube through which a gas or the like flows.

Other configurations may be modified in various ways without departing from the spirit of the present disclosure.

According to the present disclosure in some embodiments, it is possible to provide a cell culture device in which an extra length of a liquid tube connected to a liquid port is properly set. In addition, it is possible to reduce an amount of liquid remaining in the liquid tube.

While certain embodiments have been described, these embodiments have been presented by way of example only, and are not intended to limit the scope of the disclosures. Indeed, the embodiments described herein may be embodied in a variety of other forms. Furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures.

What is claimed is:

1. A cell culture device, comprising:
- a base;
- a rotary table attached to the base and capable of rotating around a first axis;
- a container holding member attached to the rotary table and capable of rotating around a second axis, the container holding member being configured to hold a cell culture container; and
- a driver configured to rotationally drive the rotary table around the first axis and to rotationally drive the container holding member around the second axis,
- wherein a liquid port to which a liquid tube is connected is arranged on an outer peripheral surface of the cell culture container,
- wherein a first predetermined portion of the liquid tube, which is spaced apart by a predetermined length from a connection portion connected to the liquid port, is positioned on the container holding member by a first positioning member,
- wherein a second predetermined portion of the liquid tube, which is further spaced apart from the connection portion than the first predetermined portion, is positioned on the rotary table by a second positioning member,
- wherein the first positioning member is configured to hold the first predetermined portion and is rotatably attached to the container holding member to be rotatable with respect to the container holding member, and
- wherein the first positioning member is spaced apart from the second axis.

2. The cell culture device of claim 1, wherein a third predetermined portion of the liquid tube, which is closer to the connection portion than the first predetermined portion, is positioned on the container holding member by a third positioning member.

3. The cell culture device of claim 2, wherein the first predetermined portion and the third predetermined portion are positioned on the same plane with respect to the container holding member.

4. The cell culture device of claim 3, wherein the driver is configured to rotationally drive the rotary table and the container holding member so that in a liquid drainage operation for draining a reagent from the cell culture container, the reagent flowing out from the liquid port into the liquid tube flows in the liquid tube in a direction away from the liquid port under a gravitational force acting on the reagent.

5. The cell culture device of claim 1, wherein the driver is configured to rotationally drive the rotary table and the container holding member so that in a liquid drainage operation for draining a reagent from the cell culture container, the reagent flowing out from the liquid port into the liquid tube flows in the liquid tube in a direction away from the liquid port under a gravitational force acting on the reagent.

6. The cell culture device of claim 1, wherein a distance between the first positioning member and the second positioning member changes as the container holding member rotates.

7. The cell culture device of claim 6, wherein the first positioning member is configured to rotate with respect to the container holding member as the distance changes.

8. A cell culture system, comprising:
- a liquid storage configured to store a liquid; and
- a cell culture device in which cells in the liquid are cultured,
- wherein the cell culture device accommodates a plurality of cell culture containers while a closed system line is maintained,
- wherein the cell culture device comprises, for each of the plurality of cell culture containers:
  - a base;
  - a rotary table attached to the base and capable of rotating around a first axis;
  - a container holding member attached to the rotary table and capable of rotating around a second axis, the container holding member being configured to hold one of the plurality of cell culture containers; and
  - a driver configured to rotationally drive the rotary table around the first axis and to rotationally drive the container holding member around the second axis, wherein a liquid port to which a liquid tube is connected is arranged on an outer peripheral surface of each of the plurality of cell culture containers, wherein a first predetermined portion of the liquid tube, which is spaced apart by a predetermined length from a connection portion connected to the liquid port, is positioned on the container holding member by a first positioning member, wherein a second predetermined portion of the liquid tube, which is further spaced apart from the connection portion than the first predetermined portion, is positioned on the rotary table by a second positioning member, wherein the first positioning member is rotatably attached to the container holding member, wherein each of the plurality of cell culture containers includes a plurality of shelves, wherein each of the plurality of shelves includes a shelf surface and a side surface configured to partition a shelf space in which the liquid is stored, wherein a communication portion is provided at a corner portion on a side of one end edge of each of the plurality of shelves, and wherein a vertical wall, which has a height lower than a height of the side surface, is provided at a boundary between the communication portion and the shelf surface of each of the plurality of shelves such that the liquid is stored in the shelf space when the shelf surface is in a horizontal state, and the liquid is drained out of the shelf space when the shelf surface is tilted.

9. The cell culture system of claim 8, wherein the first positioning member is configured to hold the first predetermined portion and is rotatably attached to the container holding member to be rotatable with respect to the container holding member.

10. The cell culture system of claim 8, wherein while the plurality of cell culture containers maintain the closed system line, a posture of each of the plurality of cell culture containers is changed to supply the liquid to each of the plurality of shelves and to drain the liquid from each of the plurality of shelves.

11. The cell culture system of claim 8, further comprising an intermediate processor including at least one of an analyzer configured to analyze a state of the cells or an adjuster configured to adjust a dilution degree of the liquid containing the cells, wherein lines in the intermediate processor constitute the closed system line.

12. A cell culture method by using a cell culture system, wherein the cell culture system comprises:

a liquid storage configured to store a liquid;

a cell culture device in which cells in the liquid are cultured;

an intermediate processor, wherein the cell culture device accommodates a plurality of cell culture containers while a closed system line is maintained, wherein the cell culture device comprises, for each of the plurality of cell culture containers:

a base;

a rotary table attached to the base and capable of rotating around a first axis;

a container holding member attached to the rotary table and capable of rotating around a second axis, the container holding member being configured to hold one of the plurality of cell culture containers; and a driver configured to rotationally drive the rotary table around the first axis and to rotationally drive the container holding member around the second axis, wherein a liquid port to which a liquid tube is connected is arranged on an outer peripheral surface of each of the plurality of the cell culture containers, wherein a first predetermined portion of the liquid tube, which is spaced apart by a predetermined length from a connection portion connected to the liquid port, is positioned on the container holding member by a first positioning member, wherein a second predetermined portion of the liquid tube, which is further spaced apart from the connection portion than the first predetermined portion, is positioned on the rotary table by a second positioning member, wherein the first positioning member is rotatably attached to the container holding member, wherein the cell culture method comprises:

preparing the liquid in the liquid storage;

transferring the liquid from the liquid storage to the plurality of cell culture containers of the cell culture device;

culturing the cells in each of the plurality of cell culture containers;

taking out the cultured cells from each of the plurality of cell culture containers; and performing, by the intermediate processor, an intermediate process on the liquid taken out from each of the plurality of cell culture containers before recovering the cells, wherein each of the plurality of cell culture containers includes a plurality of shelves, wherein each of the plurality of shelves includes a shelf surface and a side surface configured to partition a shelf space in which the liquid is stored, wherein a communication portion is provided at a corner portion on a side of one end edge of each of the plurality of shelves, and wherein a vertical wall, which has a height lower than a height of the side surface, is provided at a boundary between the communication portion and the shelf surface of each of the plurality of shelves such that the liquid is stored in the shelf space when the shelf surface is in a horizontal state, and the liquid is drained out of the shelf space when the shelf surface is tilted.

13. The cell culture method of claim 12, further comprising:

in a state in which a shelf surface of one of the plurality of cell culture containers is arranged in a horizontal culture posture, rotating the one of the plurality of cell culture containers around the first axis in a first rotational direction such that the liquid port is located on a bottom side and around the second axis in a second rotational direction, whereby the shelf surface is erected to take a liquid supply posture;

supplying the liquid to the liquid port which is located on the bottom side;

after allowing the liquid to enter the shelf space, rotating the one of the plurality of cell culture containers around the first axis in a third rotational direction opposite to the first rotational direction; and when the liquid port becomes higher than a liquid level, rotating the one of the plurality of cell culture containers around the second axis in a fourth rotational direction opposite to the second rotational direction, whereby the shelf surface is brought into the horizontal culture posture.

14. The cell culture method of claim 12, further comprising:

in a state in which a shelf surface of one of the plurality of cell culture containers is arranged in a horizontal culture posture, rotating the one of the plurality of containers around the first axis in a first rotational direction and around the second axis in a second rotational direction such that a posture of the one of the plurality of cell culture containers is changed from the horizontal culture posture to a first liquid drainage posture in which the liquid port faces downward and the liquid in a shelf space comes out to reach the liquid port;

rotating the one of the plurality of cell culture containers around the first axis in a third rotational direction opposite to the first rotational direction and around the second axis in a fourth rotational direction opposite to the second rotational direction such that the posture of the one of the plurality of cell culture containers is changed from the first liquid drainage posture to a second liquid drainage posture to move the liquid port upward; and rotating the one of the plurality of cell culture containers around the first axis in the first rotational direction and around the second axis in the second rotational direction such that the posture of the one of the plurality of cell culture containers is changed from the second liquid drainage posture to a third liquid drainage posture to move the liquid port downward, to thereby remove the liquid from an inside of the liquid tube.

15. The cell culture method of claim 12, wherein the intermediate process comprises analyzing a state of the cells by an analyzer included in the intermediate processor, before recovering the cells.

16. The cell culture method of claim 12, wherein the intermediate process comprises adjusting a dilution degree of the liquid containing the cells by an adjuster included in the intermediate processing part, before recovering the cells.

* * * * *